United States Patent
Haeg et al.

(10) Patent No.: US 7,187,974 B2
(45) Date of Patent: Mar. 6, 2007

(54) ULTRASONICALLY WELDED, STAKED OR SWAGED COMPONENTS IN AN IMPLANTABLE MEDICAL DEVICE

(75) Inventors: Daniel C. Haeg, Champlin, MN (US); Craig L. Wiklund, Bloomington, MN (US); James F. Kelley, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 678 days.

(21) Appl. No.: 10/199,601

(22) Filed: Jul. 19, 2002

(65) Prior Publication Data

US 2003/0040780 A1   Feb. 27, 2003

Related U.S. Application Data

(60) Continuation-in-part of application No. 09/767,796, filed on Jan. 23, 2001, now abandoned, which is a continuation of application No. 09/417,157, filed on Oct. 12, 1999, now abandoned, which is a continuation of application No. 09/159,119, filed on Sep. 23, 1998, now Pat. No. 6,205,358, which is a division of application No. 08/904,636, filed on Aug. 1, 1997, now abandoned.

(51) Int. Cl.
*A61N 1/375* (2006.01)
(52) U.S. Cl. .......................................... 607/36; 607/37
(58) Field of Classification Search ............ 607/36–38, 607/1, 2
See application file for complete search history.

(56) References Cited

U.S. PATENT DOCUMENTS 3,842,842 A * 10/1974 Kenny et al. .................. 607/36

(Continued)

FOREIGN PATENT DOCUMENTS

WO    WO 00/33901    6/2000

OTHER PUBLICATIONS

DVS, Technical Committee, "Ultrasonic Joining of Moulded Parts and Semi-Finished Parts of Thermo-Plastic Polymers in Mass Production: Forming with ultrasound, staking, swaging and tamping (Guideline DVS 2216, Part 3, 1992), "*Welding in the World/Le Soudage dans le Monde*, vol. 31, No. 3, p. 205-207 (1993).

(Continued)

*Primary Examiner*—George R. Evanisko
(74) *Attorney, Agent, or Firm*—Girma Wolde-Michael; Paul H. McDowall

(57) ABSTRACT

The present invention generally relates to an improved implantable medical device (IMD) and more particularly to an ultrasonically weld perforated lid for an IMD to form a hermetic seal between the IMD and the perforated lid. Appropriately configured perforated lids retain one or more components within a cavity or port formed in a part of an IMD. Such lids preferably secure a pierceable resilient grommet, septum or other resilient member in a cavity or port. When an adjustment instrument, a pull tool or a syringe is temporarily inserted therethrough and later extracted, the resilient member heals (i.e., seals and/or reseals). Preferably, the resilient member abuts a mechanical stop and is compressed slightly during assembly and ultrasonic welding of the lid. The resilient member preferably has a lateral dimension like the cavity or port so that when the lid compresses the resilient member it expands slightly and contacts the interior cavity surfaces thus improving the seal.

11 Claims, 13 Drawing Sheets

U.S. PATENT DOCUMENTS

| | | | |
|---|---|---|---|
| 4,041,956 A | 8/1977 | Purdy et al. | |
| 4,072,154 A | 2/1978 | Anderson et al. | |
| 4,142,532 A | 3/1979 | Ware | |
| 4,182,345 A | 1/1980 | Grose et al. | |
| 4,445,511 A * | 5/1984 | Cowdery et al. | 607/37 |
| 4,821,723 A | 4/1989 | Baker et al. | |
| 5,131,388 A | 7/1992 | Pless et al. | |
| 5,144,949 A | 9/1992 | Olson | |
| 5,158,078 A | 10/1992 | Bennett et al. | |
| 5,199,428 A | 4/1993 | Obel et al. | |
| 5,207,218 A | 5/1993 | Carpentier et al. | |
| 5,282,841 A | 2/1994 | Szyszkowski | |
| 5,312,453 A | 5/1994 | Shelton et al. | |
| 5,314,430 A | 5/1994 | Brady | |
| 5,330,507 A | 7/1994 | Schwartz | |
| 5,331,966 A | 7/1994 | Bennett et al. | |
| 5,354,316 A | 10/1994 | Keimel | |
| 5,431,695 A | 7/1995 | Wiklund et al. | |
| 5,456,698 A | 10/1995 | Byland et al. | |
| 5,509,928 A | 4/1996 | Acken | |
| 5,522,861 A | 6/1996 | Sikorski et al. | |
| 5,535,097 A | 7/1996 | Ruben et al. | |
| 5,545,186 A | 8/1996 | Olson et al. | |
| 5,558,641 A * | 9/1996 | Glantz et al. | 604/288.02 |
| 5,833,654 A * | 11/1998 | Powers et al. | 604/93.01 |
| 5,851,221 A | 12/1998 | Rieder et al. | |
| 5,871,514 A | 2/1999 | Wiklund et al. | |
| 6,080,188 A | 6/2000 | Rowley et al. | |
| 2001/0034543 A1 | 10/2001 | Haeg et al. | |
| 2004/0122481 A1* | 6/2004 | Tidemand et al. | 607/37 |
| 2004/0215282 A1* | 10/2004 | Weijden et al. | 607/37 |

OTHER PUBLICATIONS

Product Sheet, "*Designing Parts for Ultrasonic Welding*," Branson Ultrasonics Corporation, Danbury, Connecticut, Technical Information PW-3 (1975, printed and revised Feb. 1996).

Branson Ultrasonics Corporation, "*Textured Surface Technology*", Apr. 1995.

Branson Ultrasonics Corporation, "*Ultrasonic Staking*" Technical Information PW-6, revised Feb. 1996.

Branson Ultrasonics Corporation, "*Textured Surface Technology*" Technical Information TL-4 (1975, printed Apr. 1996).

Branson Ultrasonics Corporation, "*Ultrasonic Stud Welding*" Technical Information PW-5 (1978, printed Apr. 1996).

Kaneko, Seiji, et al., "*Ultrasonic Pressing of Plastic-Film Capacitor*" Ultrasonics International 93, Conference Proceedings, p. 699-703 (1993).

\* cited by examiner

ULTRASONICALLY WELDED, STAKED OR SWAGED COMPONENTS IN AN IMPLANTABLE MEDICAL DEVICE

CROSS-REFERENCE TO RELATED APPLICATIONS

This application is a continuation in part of U.S. patent application Ser. No. 09/767,796 filed Jan. 23, 2001, now abandoned which is a continuation of application Ser. No. 09/417,157 filed Oct. 12, 1999 now abandoned, which is a continuation of U.S. patent application Ser. No. 09/159,119 filed Sep. 23, 1998, now U.S. Pat. No. 6,205,358, which is a divisional of application Ser. No. 08/904,636 filed Aug. 1, 1997, now abandoned.

The applicants hereby incorporate the contents of U.S. Pat. No. 6,205,358 to Haeg et al., which is a divisional of application Ser. No. 09/904,636 filed Aug. 1, 1997 and U.S. Pat. No. 5,371,514 to Wiklund et al.

FIELD OF THE INVENTION

The present invention relates to apparatus and methods for use in conjunction with producing an implantable medical device (IMD); and more particularly, to various means for ultrasonically welding, swaging or staking a perforated thermoplastic component to fluidly seal a manually accessible port formed in a thermoplastic portion of an IMD.

BACKGROUND OF THE INVENTION

The earliest IMDs, e.g., implantable cardiac pacemakers and other body tissue stimulating devices, were formed of an implantable pulse generator (IPG) and a set of electrical leads attached between the IPG and heart or body tissue to be paced or stimulated. Typically, the IPG electrical circuit was powered either by Hg—Zn batteries or by induction of energy transmitted transcutaneously from a skin surface RF power generator and supplied electrical pacing or stimulating pulses to the leads. The IPG batteries and circuits were encapsulated within an epoxy compound partly for ease of manufacture and to allow hydrogen emitted by the Hg—Zn batteries to escape. Electrical connector pins and rings, if present, were initially permanently attached to the circuits. Other early IMDs, e.g. implantable monitors and cochlear implants or the like were also formed in somewhat the same manner.

Such early implantable cardiac pacemakers suffered very short useful lives due to moisture ingress through the epoxy and causing electrical dendritic growth across, and shorting of, adjacent points of the circuit, battery terminals, or discrete transistor terminals. In addition, pacing leads frequently failed due to conductor stress fractures, and batteries depleted prematurely for a variety of reasons.

In the 1960's, IPG connector assemblies were formed integrally with other IPG circuit components and embedded in an epoxy housing to enable attachment of a chosen lead to the IPG circuit for initial implant or defective lead replacement purposes. These integrally formed connector assemblies typically comprised at least one metal, electrical connector block encapsulated therein that were aligned in relation to an elongated lead end receptacle for receiving the proximal lead end. Each connector block was formed to have a bore to receive the lead connector pin or ring, depending on the type of lead intended to be used, and a threaded cross bore receiving a trapped setscrew. The electrical connections in connector blocks were typically directly attached to IPG circuits. A silicone rubber suture boot was placed in a mold in alignment with an elongated receptacle. The entire IPG, including connector assembly components, was then encapsulated in epoxy.

In use, a proximal lead connector end was inserted into the appropriate lead connector receptacle until the lead connector pin or ring was received in the bore of the connector block. A setscrew was then tightened by a hex wrench to establish firm electrical and mechanical connections and the opening through the molded epoxy housing to access the setscrew was sealed. Sutures were tied around the suture boot for sealing engagement against the lead body.

Beginning in the 1970s, hermetically sealed lithium batteries and miniaturized digital and analog integrated circuits (ICs) have been used in IMDs, particularly for implantable cardiac pacemaker and nerve stimulation IPGs. Integrated circuits, batteries and other components were enclosed in hermetically sealed metallic enclosures or "cans" separated from the connector assembly components. Electrical connection between connector blocks and other components of the connector assembly was generally accomplished by electrical feedthroughs supporting feedthrough pins extending through the hermetically sealed can.

Lead connector assembly components external to the hermetically sealed enclosure are still to this date attached to an attachment surface thereof using an in situ molding process to seal the connector assembly components and form the receptacle for a lead or catheter proximal end, etc. For example, in the formation of a lead connector assembly for a cardiac pacemaker IPG, the connector blocks and feedthrough pins are welded together and laid out in a mold with respect to any other associated components and mold plugs. An encapsulating compound is injected into the mold to form the connector header assembly molded to the IPG attachment surface as described, for example, in U.S. Pat. No. 4,041,956, the disclosure of which is hereby incorporated by reference herein in its entirety. This approach is time consuming and not terribly precise. If the resulting connector header assembly fails to meet dimensional tolerances or other quality requirements, it is difficult to rework the IPG.

In 1979 the MEDTRONIC® SPECTRAX® cardiac pacemaker IPGs were introduced having the digital and analog or hybrid ICs and lithium batteries enclosed within a hermetically sealed titanium enclosure having feedthroughs extending through an enclosure attachment surface thereof. Assembly of these components and other details are disclosed in U.S. Pat. Nos. 4,142,532 and 4,182,345, hereby incorporated by reference herein in their respective entireties.

The lead connector assembly, in this case and as used in IPG models to the present time by Medtronic, Inc., is manufactured as a separate pre-formed connector header module that encloses connector components and is attached to an enclosure attachment surface of the hermetically sealed enclosure and to the feedthrough pins. The connector header module is molded of a thermoplastic elastomer such as medical grade polyurethane, has an outer module surface and a number of receptacles and channels disposed within it that in some instances are accessible through windows, channels or recesses extending outwardly to the module surface. The connector header module receives the electrical connector blocks in connector block receptacles such that the connector block bores are aligned with elongated lead connector receptacles for receiving the proximal lead connector end assemblies. In a typical design, each such connector block is formed with a threaded cross bore receiving a trapped setscrew as described above. Each setscrew of each connector block in a connector block receptacle is also aligned with a septum receptacle for receiving a silicone rubber setscrew septum.

A pre-formed connector header module is generally formed with pin channels for directing the feedthrough pins into contact with the respective connector blocks and with windows to allow the connector blocks and septums to be inserted into their respective receptacles. In each case, the connector block receptacle window or a further window to the module surface is provided for allowing the feedthrough pin end to be welded to the connector block. The windows and pin channels are typically back filled with a medical grade silicone adhesive after the welding step and attachment of the connector header module to the hermetically sealed enclosure.

The receptacle for the connector block and the connector block itself most preferably have tight dimensional tolerances to permit precise alignment of the connector block bore with the lead connector receptacle. In one approach, the connector block receptacle opening dimensions are reduced and the opening edge thereof shaped so that the connector block stretches the opening edge as it is inserted into the connector block receptacle. In other cardiac pacemaker IPGs, each connector block is inserted into a connector block receptacle and ultrasonic energy is applied to the edge of the connector block window to melt it over and tamp it against the exposed surface of the connector block. This ultrasonic tamping technique of dissimilar material parts is similar to that shown in the article entitled "Ultrasonic Joining of Moulded Parts and Semi-Finished Parts of Thermo-Plastic Polymers in Mass Production—Forming with Ultrasound," Staking, Swaging and Tamping (Guideline DVS 2216, Part 3, 1992), *Welding in the World, Le Soudage Dans Le Monde*, Vol. 31, No. 3, pp. 205–207 (1993), the disclosure of which is hereby incorporated by reference herein in its entirety.

As a general rule, a connector header module formed as described above must have tight dimensional tolerances and remain dimensionally stable over long periods of time in the hostile environment found within the human body. Any substantial initial or time-induced misalignment of the lead connector receptacle bores extending through the molded module housing and the connector block bores can make initial attachment or removal and replacement of a lead connector end impossible or unreliable. During the attachment of the connector header module to the hermetically sealed enclosure, medical grade adhesive is usually employed to attach the module attachment surface to the enclosure attachment surface. While the adhesive cures, it is necessary to ensure that the attachment surfaces are not disturbed.

Some workers in the field have proposed employing mechanical attachment mechanisms as a substitute for, or in addition to, the use of the medical grade adhesive for attaching surfaces to one another. Mechanical attachment mechanisms proposed in the art for use with or without medical grade adhesive are described in U.S. Pat. Nos. 4,142,532 and 4,182,345, both incorporated herein by reference in their respective entireties. While the approaches described in those patents have merit, they require the use of additional precision piece parts and assembly steps that may add to the cost and time required to assemble the connector header module and connect it to the hermetically sealed enclosure.

Finally, it should be noted that it has been recently proposed to form the connector header module as part of a shroud surrounding and adhering to the rim of the hermetically sealed enclosure in order to simplify the assembly by reducing the number of parts, assembly steps and dimensional tolerance requirements. Such configurations are shown in U.S. Pat. Nos. 5,535,097, 5,522,861, 5,456,698 and 5,431,695, all incorporated herein by reference in their respective entireties. In such configurations, the shroud is preferably formed of a flexible silicon rubber and pacing leads may be attached and replaced in conventional fashion. The use of silicone rubber presents certain difficulties and disadvantages, however, most of which relate to dimensional instability and lack of rigidity, lack of an aesthetically pleasing physical appearance and potential discoloration of the silicone rubber during storage and sterilization.

Furthermore, similar tight dimensional tolerance requirements for IMDs such as drug pumps and the like are required so that the therapeutic, diagnostic or other fluid(s) retained within said pumps are retained until needed. Furthermore, periodic replenishment of the fluid reservoir of such pumps typically requires a resilient septum member through which said fluid is injected. Septum members of implantable drug delivery vehicles therefore may also benefit from the teaching of the present invention.

A common phenomenon of materials such as polyurethane which were previously adhesively bonded to form a header component for an IMD, is that wax-like materials rise to the surface of the polyurethane. Such wax-like materials must be removed so that medical grade adhesive materials can be used to connect the header components. Multi-step wax removal processes were used in which detergents and solvents were applied and removed, thereby adding incremental costs and additional time to the IMD manufacturing process. Such removal processes were typically temporary. That is, the wax-like material would spontaneously "bloom" within approximately 24 hours and if the IMD was not fully constructed, the wax removal process must be repeated. In addition, medical grade adhesive typically requires several hours to adequately cure, further reducing the interval in which an IMD may be manufactured.

SUMMARY OF THE INVENTION

The present invention provides solutions to at least some of the problems existing in the prior art such as: (a) highly precise dimensional tolerances being required for injection mold tools employed to form connector or header module components, or connector or header modules; (b) excessive flash occurring in connector or header module components, or connector or header modules, formed by injection molding means; (c) hand trimming of flash being required in connector or header module components, or connector or header modules, formed by injection molding means; (d) backfilling of voids, channels and the like with medical grade adhesive being required in connector or header module components, or connector or header modules; (e) molded parts or components having flash disposed thereon having decreased biocompatibility; (f) medical adhesive requiring long cure times; (g) hand assembly or reworking steps being required to complete assembly of header or connector modules; (h) parts or components requiring preparation to permit or enhance adhesion of medical adhesive to desired surfaces; (I) post-assembly steps being required for cleaning up and removing medical adhesive; and (j) medical adhesive having insufficient structural or mechanical integrity to provide mechanical protection of electrical and mechanical parts disposed with a header or connector module.

Various embodiments of the present invention have certain advantages, including, but not limited to, at least some of the following: (a) providing reduced structural complexity and dimensional tolerance requirements for injection molding tools employed to form header or connector modules or components therefor; (b) eliminating or reducing substantially the use of medical adhesives to form connector or header modules; (c) eliminating or reducing substantially the requirement for long cure times of medical adhesive; (d) providing improved mechanical protection for parts or components disposed within the header or connector module; (e) permitting the design and use of less expensive, less structurally complex, lighter, smaller and fewer parts or components for placement in a header or connector module; (f) permitting the use of parts or components in header or connector modules that have improved performance characteristics respecting similar prior art parts or components; (g) reducing manufacturing time; (h) reducing manufacturing cost; (I) providing increased manufacturing flexibility; (j) providing increased part or component interchangeability between different models of IMDs; and (k) reducing inventory costs.

In one embodiment of the present invention a recess formed in an outer surface of a connector module or header of an IMD is partially covered by a lid or cover that is ultrasonically welded around the periphery of the recess.

In one form of this embodiment, a resilient, pierceable grommet is sealingly retained in the recess adjacent a setscrew of a connector block. Structure within the recess, such as an annular step or other mechanical stop, supports the grommet at a predetermined elevation. Then, when a horn member of an ultrasonic welding apparatus contacts the lid during welding the grommet expands and seals the interior periphery of the recess. As long as the compressed grommet fluidly seals the recess, either a continuous or an intermittent weld may be formed around the periphery of the lid. However, utilizing both so-called near-field or far-field ultrasonic bonding techniques welds can be formed at different elevations relative to the exterior surface. That is, the weld may be formed near the exterior surface of the lid (and IMD) and/or at the junction between an annular step member, or other mechanical stop structure, formed at a suitable elevation within the recess.

Thus, according to the present invention, several weld- and/or compression-type seals may be formed. A first seal between the exterior surface of the lid and the exterior surface of an IMD, a second seal between the lid and an interior step member, a third seal between a protruding upper surface of the grommet and an opening formed in the lid, and a fourth seal between the sides of the grommet and the lateral interior surface of the recess. Of course, other and additional seals may be formed according to present invention. For example, several annular steps within the recess and corresponding step features of the lid and/or the grommet provide additional compression- or weld-type seals. Also, in lieu of annular steps an inner sleeve member may be used to provide a mechanical stop against which the grommet is compressed by the lid.

In another form of the invention, in lieu of a grommet a septum member is sealingly retained in the recess on a first side and fluidly seals a refill port for a fluid reservoir of an implantable drug pump. In this form, the lid preferably has a single relatively large aperture formed therein and when ultrasonically welded to the drug pump compresses the septum member against an inner plate member. The inner plate member preferably has a plurality of ports formed through the plate which are adapted to receive a syringe.

A preferred form of the lid is an annular thermoplastic washer member and the periphery portions of said lid or cover and/or the periphery of the recess preferably have energy director members disposed thereon to promote a strong weld therebetween when subjected to ultrasonic energy. Such members rapidly melt and combine with adjacent thermoplastic structure to form the ultrasonic weld. Also, in the event that a surface weld is desired between the lid and upper periphery of a recess formed in an IMD, either the lid or the periphery of the recess preferably have a flash-reducing cut-out or step into which the adjacent thermoplastic material flows during welding.

The thermoplastic header, refill port or other thermoplastic portion of an IMD body in which the recess is formed may be constructed of any suitable biocompatible thermoplastic material such as polyurethane, polysulfone, Halar® ECTFE, a copolymer of ethylene and chlorotrifluoroethylene (a type of thermoplastic fluoropolymer), that was originally produced by Allied Chemical Corporation and now is produced by Ausimont USA, Inc. of 44 Whippany Road, Morristown, N.J. Of course, any other biocompatible material which is susceptible to ultrasonic welding techniques may be used in practicing the present invention.

The grommet, septum or other resilient member is preferably fabricated of compressible silicone rubber and similar materials which can be repeatedly pierced with a thin instrument—such as a hex wrench, a syringe, a pull tool for advancing a medical lead into a connector port, and the like—and which "heal" after the instrument is removed.

An advantage of the present invention relates to the inherent modular configuration of the assembled parts. That is, for header modules having multiple connector ports, a like number of grommets, lids and, optionally, sleeve-type mechanical stop members may be used. Furthermore, such modularity allows one assembly sequence for a variety of header configurations.

As will be appreciated with reference to the drawings, and particularly in the case of the grommet assembly, a central portion of reduced thickness may be used to assist a user manually align the instrument adjustment tool and to provide slightly less insertion resistance. In addition, both the grommet and septum member preferably have a peripheral shoulder portion that corresponds to structure of the lid or cover. Also, as noted above, to reduce or eliminate post fabrication rework of the components due to excess material (e.g., "flash"), a channel or slot may be formed at the surface of and adjacent to the bonded components to receive excess material.

A fluid tight seal at the junction of the lid or cover and the periphery of the recess and/or between the grommet or septum and the wall of the recess is preferably aided by placing the grommet or septum under compression during fabrication. That is, the grommet or septum expands after fabrication to help form the fluid seal. Additional features or components, such as a mechanical stop or substantially non-compressible ring of material, may be disposed within the recess. Such a mechanical stop may comprise a perforated disk, with such perforation adapted to admit the tip of a syringe, for certain drug pump applications.

In a preferred embodiment wherein a setscrew is disposed in the recess, said setscrew is a "dog tip" type setscrew (i.e., a partially threaded shank). When such a dog tip screw is rotated counterclockwise, it remains partially inserted in a threaded bore. A halt ring coupled between the setscrew and the compressible grommet helps ensure that the screw cannot be reversed too far and thus cannot reversed through the grommet and will neither further compress the grommet nor force the lid away from the IMD.

The foregoing and other objects, advantages and features of the present invention will be appreciated better by referring to the appended claims, drawings and detailed description.

BRIEF DESCRIPTION OF THE DRAWINGS

In the drawings, which are not rendered to scale and which illustrate only a few embodiments of the present invention, like reference numbers refer to like parts.

DETAILED DESCRIPTION OF THE PREFERRED EMBODIMENTS

The preferred embodiments of the present invention relate to ultrasonic means for attaching or securing various components inside a pre-formed header module to thereby form a hermetically sealed enclosure. Implantable medical devices where the present invention finds application include implantable drug dispensers, IPGs (including cardiac pacemakers, pacemaker-cardioverter-defibrillators, nerve, muscle and neurological stimulators, cardiomyostimulators, etc.), implantable cardiac signal monitors and recorders and the like. Virtually all MEDTRONIC® electronic IMDs that require attachment of a hermetically sealed power supply and circuitry to an interchangeable catheter or electrical lead employ a general configuration of a hermetically sealed enclosure in conjunction with a pre-formed header module.

Figure 1:
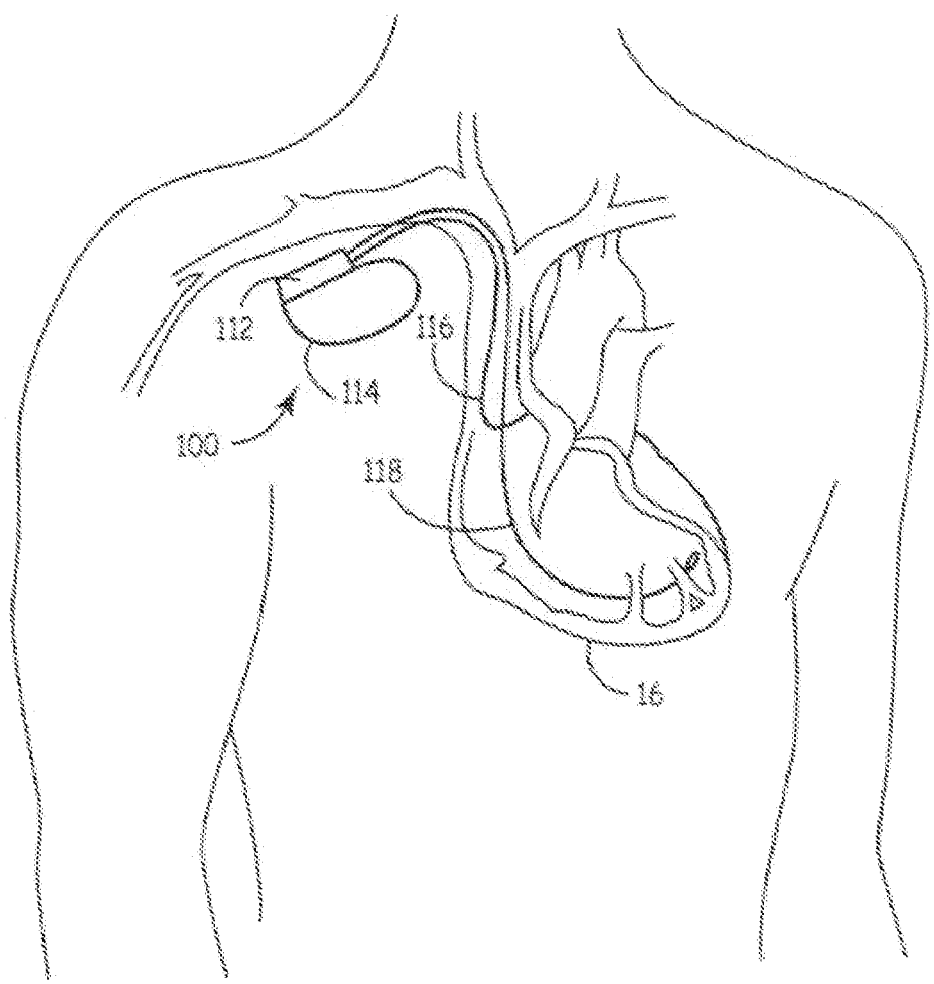
FIG. 1 shows a simplified schematic view of an IMD of the present invention disposed in a human subject.

FIG. 1 is a simplified schematic view of an IMD 100 embodying the present invention, where an improved pre-formed header module 112 is attached to a hermetically sealed enclosure 114 and implanted near human heart 16. In the case where implanted medical device 100 is a pacemaker it includes at least pre-formed header module 112 and one or both of pacing and sensing leads 116 and 118. Pacing and sensing leads 116 and 118 sense electrical signals attendant to the depolarization and re-polarization of the heart 16, and provide pacing pulses for causing depolarization of cardiac tissue in the vicinity of the distal ends thereof. Implantable medical device 100 may be an implantable cardiac pacemaker such as those disclosed in U.S. Pat. No. 5,158,078 to Bennett et al, U.S. Pat. No. 5,312,453 to Shelton et al, or U.S. Pat. No. 5,144,949 to Olson, all hereby incorporated herein by reference in their respective entireties.

Implantable medical device 100 may also be a PCD (Pacemaker-Cardioverter-Defibrillator) corresponding to any of the various commercially available implantable PCDs, with the substitution of connector module 112 of the present invention for the connector block assembly otherwise present. The present invention may be practiced in conjunction with PCDs such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless or U.S. Pat. No. 4,821,723 to Baker et al., all hereby incorporated herein by reference in their respective entireties. Those devices may be employed directly in conjunction with the present invention, and most preferably are practiced such that the feedthroughs interconnecting the circuitry therein to their connector blocks is located to permit ready access between the feedthroughs and the electrical connectors disposed within the connector bores of connector or header module 112.

Alternatively, IMD 100 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein in their respective entireties. The present invention is believed to find wide application to any form of implantable electrical device for use in conjunction with electrical leads, and is believed to be particularly advantageous in those contexts where multiple medical electrical leads are employed and desired.

In general, hermetically sealed enclosure 114 includes an electrochemical cell such as a lithium battery, circuitry that controls device operations and records arrhythmic EGM episodes, and a telemetry transceiver antenna and circuit that receives downlink telemetry commands from and transmits stored data in a telemetry uplink to the external programmer. The circuitry and memory may be implemented in discrete logic or a micro-computer based system with A/D conversion of sampled EGM amplitude values. The particular electronic features and operations of the IMD are not believed to be of overriding significance in respect of practicing the present invention. One exemplary operating system is described in commonly assigned, co-pending U.S. patent application Ser. No. 08/678,219, filed Jul. 11, 1996, for "Minimally Invasive Implantable Device for Monitoring Physiologic Events," the disclosure of which is hereby incorporated by reference herein in its entirety.

Figure 2:
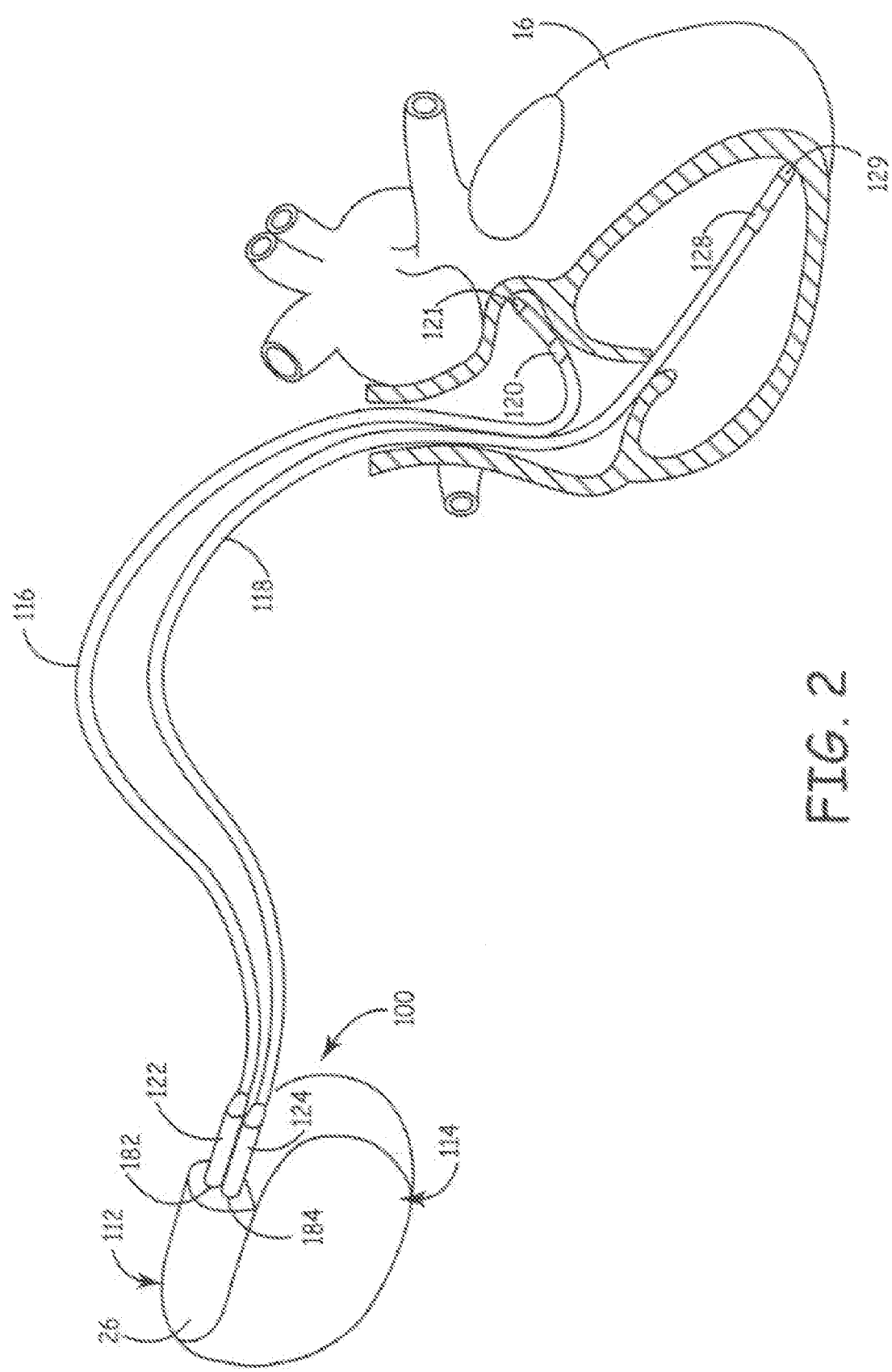
FIG. 2 shows an isometric view of a cardiac pacemaker and corresponding lead system of the present invention as they relate to a human heart.

FIG. 2 depicts connector module 112 and hermetically sealed enclosure 114 of IMD or dual chamber pacemaker IPG 100 of the present invention as they relate to patient's heart 16. Trial and ventricular pacing leads 116 and 118 extend from connector header module 112 to the right atrium and ventricle, respectively. Trial electrodes 120 and 121 disposed at the distal end of the atrial pacing lead 116 are located in the right atrium. Ventricular electrodes 128 and 129 at the distal end of ventricular pacing lead 118 are located in the right ventricle.

Connector header module 112 may take any of the forms described herein for establishing electrical and mechanical connections of proximal connector end assemblies 122 and 124 of the atrial and ventricular pacing leads 116 and 118 to electrical or electronic circuitry disposed within hermetically sealed enclosure 114. Connector header module 112 therefore preferably incorporates four connector blocks (not shown) within the module housing that are aligned with elongated lead connector end receptacles 182 and 184, and that are adapted to receive lead connector end assemblies 122 and 124. Header module 112 may be molded of a rigid thermoplastic material such polyurethane, polysulfone or any other such suitable medical grade thermoplastic material. Header module 122 has an exposed exterior surface and a number of receptacles and channels formed therein. Feedthroughs and feedthrough pins connected to the connector blocks and extending through the hermetically sealed enclosure 114 are also not shown in FIG. 2.

Figure 3:
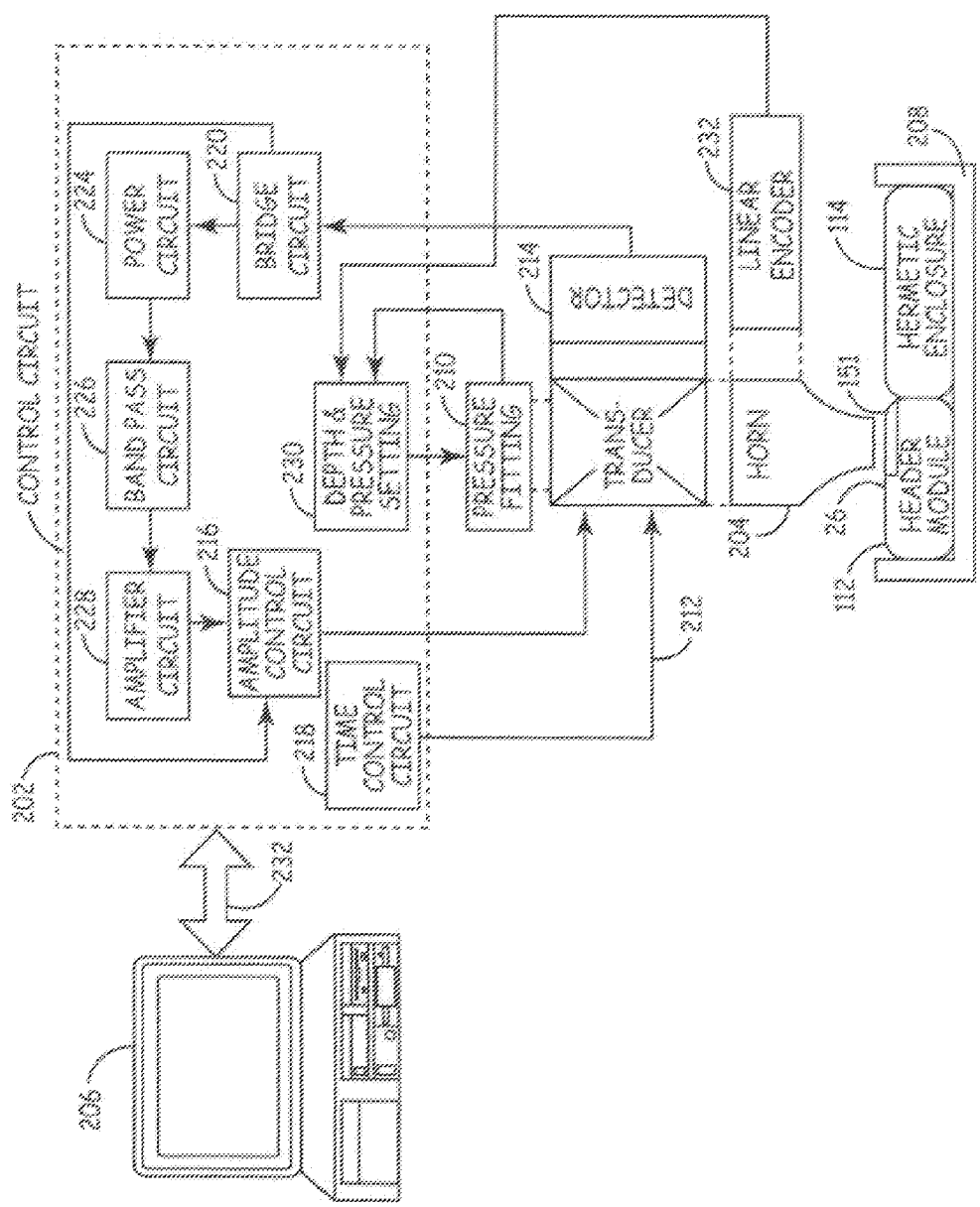
FIG. 3 shows a simplified block system diagram for employing ultrasonic welding energy in the attachment of various components, covers, lids and the like to a header module to form a hermetically sealed enclosure suitable for implantation within the human body.

FIG. 3 depicts an ultrasonic welding system and some of the manufacturing steps for ultrasonically attaching various components such as lids or covers to preformed header module 112. The system and corresponding methods of FIG. 3 are similar to those described in the article "Ultrasonic Pressing of Plastic-Film Capacitor" by S. Kaneko et al., at pp. 699–702 in *Ultrasonics International 93 Conference Proceedings*, (1993), and is representative of a computerized ultrasonic welding system sold by Branson Sonic Power Co. of Danbury, Conn. The attachment steps depicted in FIG. 3 most preferably follow the assembly and welding of the pre-formed header module to hermetically sealed enclosure 114 using upstanding tabs 152, 152', 154 and 154' and corresponding recesses as disclosed in U.S. Pat. No. 5,871,514 for "Attachment Apparatus and Method for an Implantable Medical Device Employing Ultrasonic Energy" to Wiklund et al. filed Aug. 1, 1997.

Figures 4A, 4B, 4C:
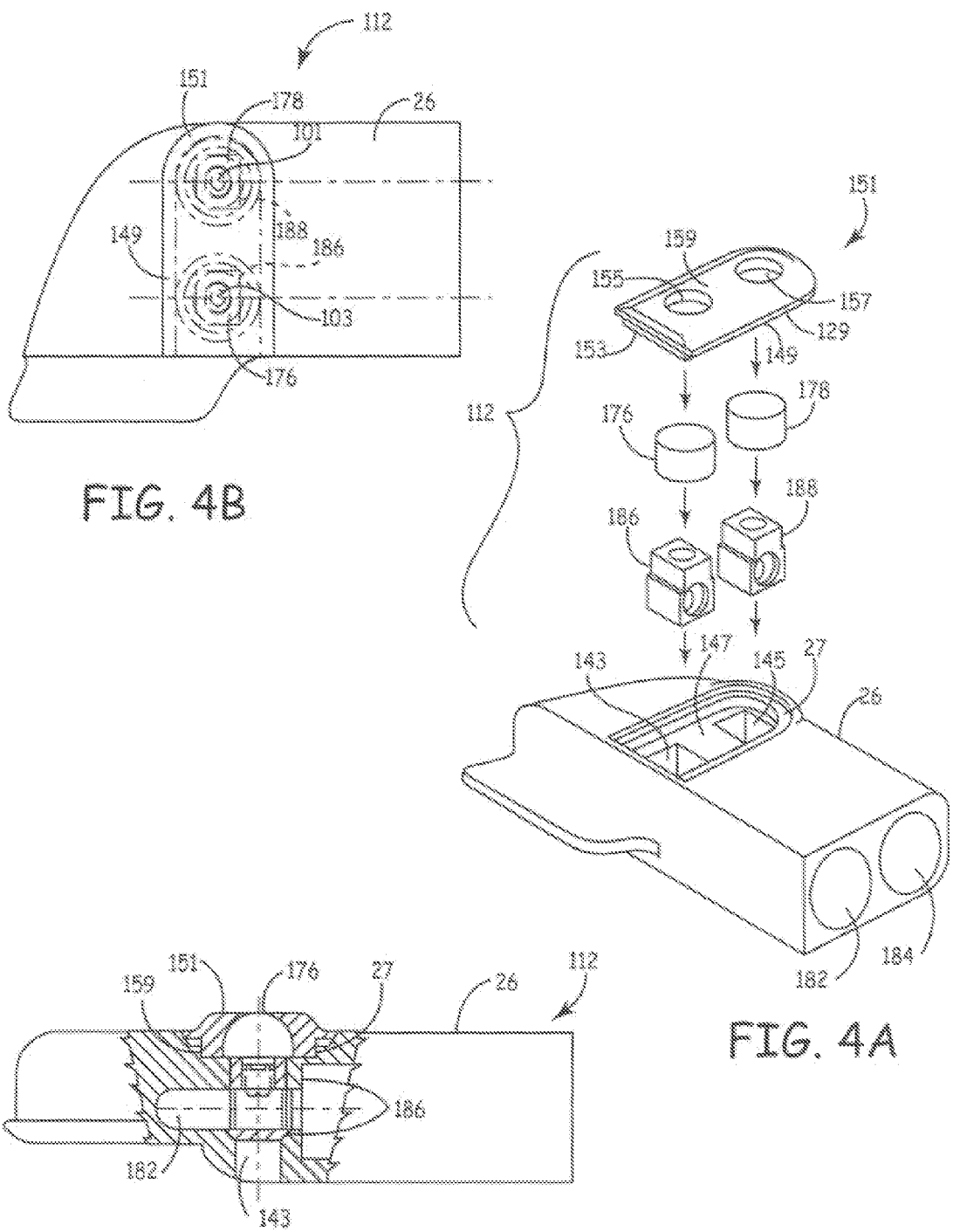
FIG. 4(a) is an exploded perspective view of one embodiment of a connector module of the present invention.
FIG. 4(b) is a top plan view of the connector module of FIG. 4(a).
FIG. 4(c) is a cross-sectional view of the connector module of FIG. 4(a).
Figure 5:
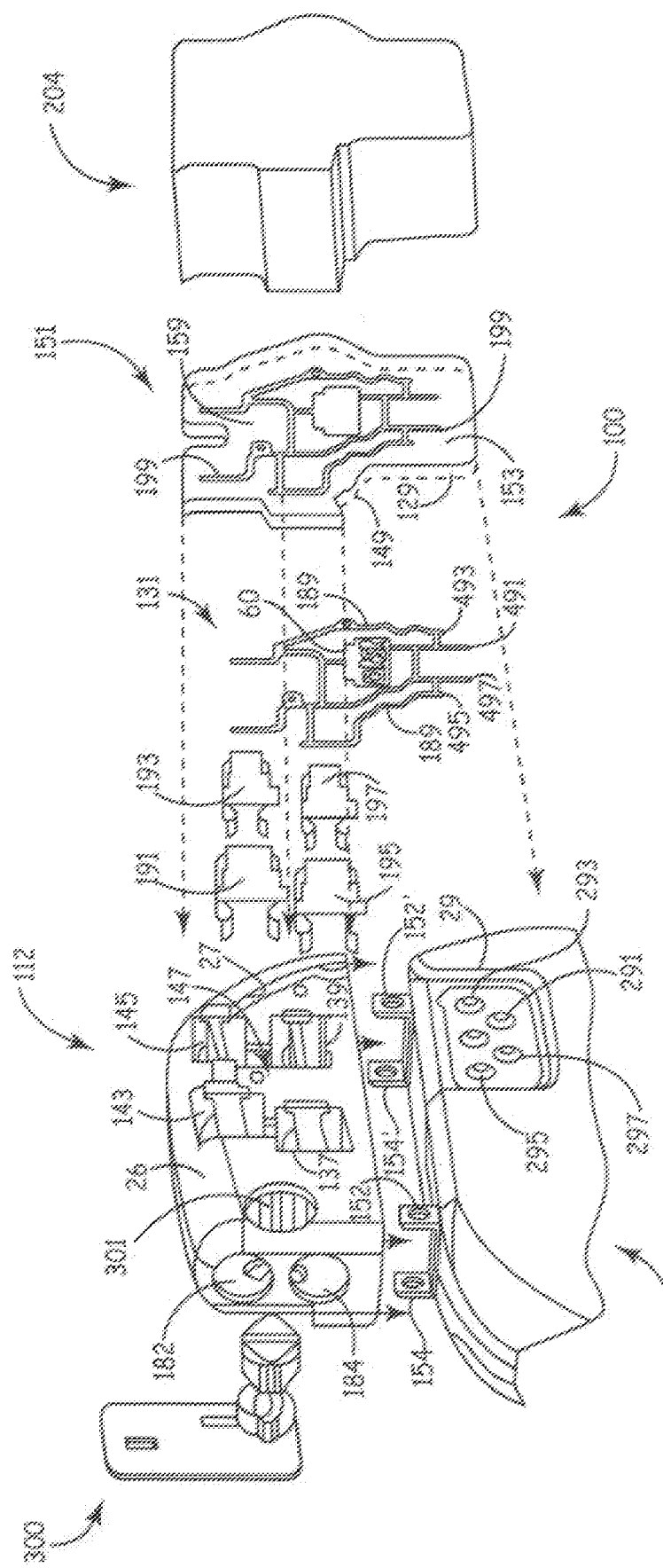
FIG. 5 is an exploded perspective view of another embodiment of a connector module and corresponding hermetically sealed IPG of the present invention.
Figure 6:
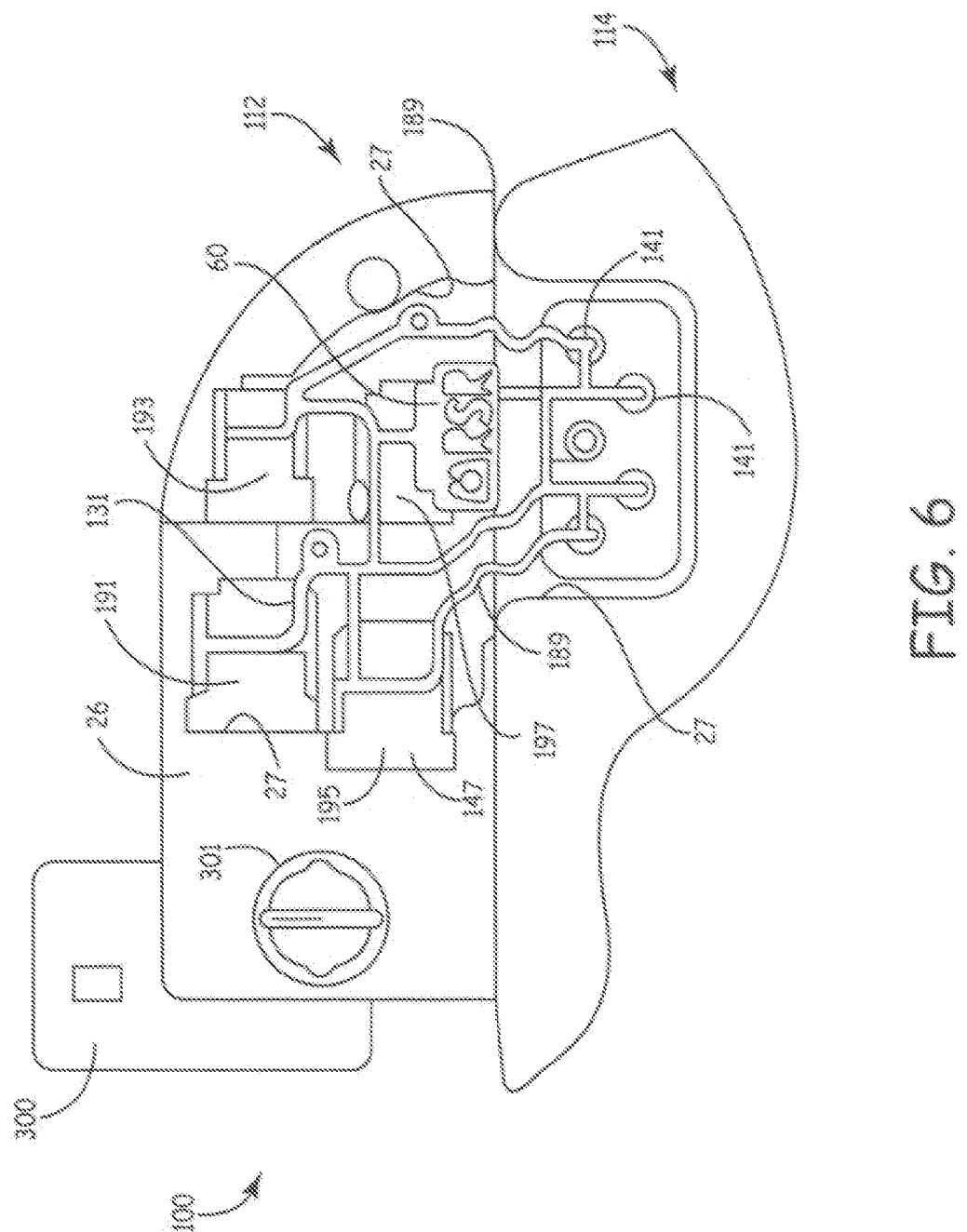
FIG. 6 is a side view of the connector module and corresponding hermetically sealed IPG of FIG. 5.

The attachment steps illustrated in FIG. 3 preferably follow attachment of the terminals of feedthrough pins 291, 293, 295 and 297 to MBCs (multiple beam contacts) 191, 193, 195 and 197 via ribbon connector 131 and subsequent removal of undesired metallization disposed between feedthrough contacts or wires 491, 493, 495 and 497 pins, as illustrated in FIGS. 5 and 6. Alternatively, the illustrated attachment steps may follow the emplacement of grommets 176 and 178 or setscrew blocks 186 and 188 within connector module 112 as illustrated in FIGS. 4(a) through 4(c).

Ultrasonic welding system 200 includes control circuit 202 for operating ultrasonic horn 204 to apply ultrasonic welding energy to the desired portions of header module 112 under the control of microprocessor based work station 206 that is controlled by a human operator. A human operator enters into workstation 206 a desired applied static force value, a desired linear travel distance, a desired ultrasonic weld time and a desired cooling time following the ultrasonic weld time. The operator may select the amplitude of the ultrasonic vibrations of ultrasonic horn 204 and the ultrasonic frequency, although these may be fixed for each weld cycle in a given configuration of ultrasonic horn 204 and header module 112.

The vibration amplitude and frequency, the applied static force, and the period of time that horn 204 applies ultrasonic energy to a desired surface or portion of header module 112 may be selected by the operator. Those factors determine the amount of ultrasonic energy delivered to connector module 112. When ultrasonic energy is delivered to the module, ultrasonic energy is converted into heat energy to melt the thermoplastic material in a desired region. In preferred embodiments of the present invention, ultrasonic energy is employed to melt a mass of thermoplastic material extending from the horn surface laterally into a pre-formed channel or groove. The volume and depth of the melted mass is controlled by the shape and surface area of the horn surface of ultrasonic horn 204 and the depth to which horn 204 penetrates beneath the exterior surface of header module 112.

As the horn surface penetrates into the surface, it moves closer to any preformed channels that may be disposed within header module 112 as the thermoplastic material melts. The area of the melt then advances into the channel to form a mass of melted thermoplastic material therein. It is desirable to control the depth of penetration to ensure that the horn surface does not transmit ultrasonic energy directly into to hermetically sealed enclosure 114. The linear travel of horn 204 is preferably set to the dimensions of a selected particular header module 112 so that applied ultrasonic energy is concentrated in a region surrounding the channels to melt the adjoining thermoplastic material therein.

Entered ultrasonic weld cycle values are translated into operating commands by work station 206, and are conveyed on bus 232 to control circuit 202. Workstation 202 may also supply commands to control the adjustment of the work piece holder 208 and horn 204 to successively locate each channel with respect to the horn surface for each ultrasonic weld cycle. In the weld operating cycle, header module 112 and lid or cover 151 are preferably seated together as shown in FIG. 3 and fitted into work piece holder 208 adjacent ultrasonic horn 204. Contact of the horn surface with the exterior surface of the header module 112 is then established.

Ultrasonic horn 204 is mounted to a pressure fitting 210 controlled by pressure setting circuit 230 to apply a precisely controlled static force of the horn end surface against the outer surface 26 of header module 112 and outer surface 159 of cover or lid 151 positioned at lid recess 147 and disposed on header module surface 26. Emitter or transducer 212 is coupled between pressure fitting 210 and ultrasonic horn 204 and vibrates horn 204 at a predetermined ultrasonic frequency and amplitude and for a predetermined period of time set by time control circuit 218. At the expiration of the predetermined period of time, a cooling time is prescribed before horn 204 is retracted from header module 112 and before the next weld cycle is commenced.

In the ultrasonic welding process, horn 204 is brought into contact with surface 26 and cover 159 at a predetermined static pressure. The applied static pressure is controlled by depth and pressure setting module 230 that responds to a static pressure value command provided by workstation 206 for operating pressure-fitting 210 to advance the horn surface against surface 26 and cover 159. An appropriate feedback control signal may be applied to depth and pressure setting module 230. Pressure fitting 210 also controls the penetration depth of the horn 204 into surface 26 of connector module 112 and cover 159 as ultrasonic vibrations are converted into heat energy to melt the thermoplastic material. Control of penetration depth is effected through feedback from linear encoder 232 coupled to horn 204, transducer 212 and pressure fitting 210. The output signal of linear encoder 232 is reset when the static pressure is first applied. The advancement of horn 204 from the initial position is measured and quantified as ultrasonic energy melts the thermoplastic material. When an output signal provided by linear encoder 232 signifies that the desired penetration depth has been is achieved or will be achieved within a certain short period of time, depth and pressure setting module 230 terminates the delivery of pressure to and advancement of horn 204.

During the application and delivery of ultrasonic energy, the amplitude of the ultrasonic vibrations is controlled by amplitude control circuit 216, which responds to input amplitude commands and a processed feedback signal from amplitude detector 214. The amplitude-setting signal is applied by an amplitude control circuit to transducer 212, which in turn vibrates horn 204 at a prescribed ultrasonic frequency and amplitude. During the period of time during which ultrasonic welding occurs, the amplitude of the delivered ultrasonic signal is measured and converted to a feedback signal by detector 214. That feedback signal is applied to bridge circuit 220 for comparison to the prescribed amplitude. A difference signal is generated by the bridge circuit 224 that is processed, filtered and amplified by a power circuit 224, filter circuit 226 and amplifier circuit 228 and applied to the amplitude control circuit 216 to modify the amplitude output signal applied to the transducer 212.

Further details and information concerning ultrasonic welding methods, techniques, materials and the like are set forth in the following publications distributed by Branson Ultrasonics Corporation of Danbury, Conn., each such publication hereby being incorporated by reference herein in its respective entirety: (a) "Designing Parts for Ultrasonic Welding," Technical Information PW-3, © Branson Ultrasonics Corporation, 1975, printed and revised February, 1996; (b) "Ultrasonic Stud Welding," Technical Information PW-5, © Branson Ultrasonics Corporation, 1978, printed April, 1996; and (c) "Textured Surface Technology," TL4, © Branson Ultrasonics Corporation, 1975, printed April, 1995. The foregoing publications provide useful information concerning various types of ultrasonic weld joints and techniques such as tongue and groove joints, step joints, textured surfaces, criss-cross joints, specialized joints, shear joints, stud welding, staking techniques, standard profile stakes, low profile stakes, dome stakes, knurled stakes, flush stakes, hollow stakes and high pressure stakes, all of which find application in various embodiments of the present invention.

FIGS. 4(*a*) through 6 show two different embodiments of the present invention, where various header module components are trapped or otherwise secured within header or connector module 112 by ultrasonically welded lid or cover 151. Lid or cover 151 is most preferably formed but not necessarily of the same material as connector or header module 112. Suitable materials for forming connector or header module and lid or cover 151 include medical grade polyurethane, polysulfone and other polymers suitable for implantation within the human body and susceptible to ultrasonic processes.

FIGS. 4(*a*) through 4(*c*) show selected views of header module 112 from exploded and assembled top and cross-sectional perspectives, where setscrew connector blocks 186 and 188 and grommets 176 and 178 are disposed in corresponding recesses 143, 145 and 147, and secured therewithin by cover 151. Cover or lid 151 is ultrasonically welded to surface 26 of connector module 112 along connector module lip or channel 27 such that initially molten plastic forms and solidifies between cover recess periphery 27 and cover peripheral edge 129 or step 149. Horn 204 (not shown in FIGS. 4(*a*) through 4(*c*)) covers and is applied to top or outer surface 159 of cover 151 and the region surrounding lip or channel 27 of connector module 112 during the ultrasonic welding process described hereinabove. Cover 151 and corresponding cover recess 147 are preferably configured such that cover peripheral edge 129 or step 149 matingly engage through tongue and groove joint, step joint or shear joint structural means with corresponding structural means disposed along or in cover recess periphery 27. Other structural means known in the art of ultrasonic welding may also be employed to permit ultrasonic bonding between cover 151 and connector module 112. Medical adhesive may optionally be emplaced between cover 151 and the bottom surface of recess 147 prior to the ultrasonic welding step to provide additional, and highly desirable, increased path length for any bodily fluids that might ingress between cover 151 and connector module 112, and thereby minimize the possibility of an electrical short developing between the setscrew connector blocks, for example.

Grommets 176 and 178 are compressed between lower surface 153 of cover 151 and the bottom surface forming cover recess 147 disposed within outer surface 26 of connector module 112. Setscrew connector blocks 186 and 188 accept the proximal ends of leads 118 and 116 therewithin, and thereby establish mechanical and electrical connection between the leads and IMD 100. Setscrews integral to connector blocks 186 and 188 may be turned and tightened against those distal lead ends by pushing an appropriately configured allen wrench through recesses 155 or 157 and compressible grommets 176 and 178 into setscrew recesses 101 and 103. Ultrasonic welding of cover 151 to connector module 112 may eliminate the need to use medical grade adhesive to secure grommets 176 and 178 to connector module 112 and provides other advantages described hereinabove.

FIG. 5 shows another embodiment of the present invention, where multi-beam connectors (MBCs) 191, 193, 195 and 197 are disposed in corresponding recesses 143, 145, 137 and 139 formed in connector module 112, and secured therewithin by cover 151. Cover or lid 151 is ultrasonically welded to surface 26 of connector module 112 along connector module lip or channel 27 such that initially molten plastic forms and solidifies between cover recess periphery 27 and cover peripheral edge 129 or step 149. Horn 204 covers and is applied to top or outer surface 159 of cover 151 and the region surrounding lip or channel 27 of connector module 112 during the ultrasonic welding process described hereinabove.

Cover 151 and corresponding cover recess 147 are preferably configured such that cover peripheral edge 129 or step 149 matingly engage through tongue and groove joint, step joint or shear joint structural means with corresponding structural means disposed along or in cover recess periphery 27. Other structural means known in the art of ultrasonic welding may also be employed to permit ultrasonic bonding between cover 151 and connector module 112. Medical adhesive may optionally be emplaced between cover 151 and recess 147 prior to the ultrasonic welding step to provide additional, and highly desirable, increased path length for any bodily fluids that might ingress between cover 151 and connector module 112, and thereby minimize the possibility of an electrical short developing between feedthrough wire contacts 491, 493, 495 and 497 integral to ribbon connector 131, feedthrough pins 191, 293, 295 and 297, and MBCs 191, 193, 195 and 197, for example.

In those areas where the bottom portions of cover 151 overlap onto and over the feedthrough pin portions of hermetically sealed enclosure 114, cover 151 is generally not ultrasonically welded to enclosure 114. This is because enclosure 114 is usually formed from a biocompatible metal such as titanium, whereas cover 151 is generally formed from a thermoplastic material, and the two dissimilar materials forming cover 151 and enclosure 114 may not be ultrasonically welded to one another. In some embodiments of the present invention, however, cover 151 and enclosure 114 are formed of mutually ultrasonically weldable thermoplastic or polymeric materials.

The embodiment of the present invention shown in FIGS. 5 and 6 eliminates grommets 176 and 178, setscrew connector blocks 186 and 188 and a separately supplied allen wrench described in conjunction with FIGS. 4(*a*) through 4(*c*) hereinabove. In their stead MBCs 191, 193, 195 and 197, tool 300 and recess 301 are employed as described in further detail in above-referenced U.S. patent application Ser. No. 08/877,033 for "Attachment Apparatus and Method for an Implantable Medical Device Employing Ultrasonic Energy" to Rowley.

Inwardly-facing surface 153 of cover 151 and corresponding outwardly-facing portions of cover recess 147 matingly engage and trap ribbon connector 131 and radio-opaque marker 60 therebetween. Channels, voids and recesses 199 are preferably formed in inwardly facing surface 153 of cover 151 to matingly accept ribbon connector 131 and integral radio-opaque marker 60 therewithin. Ultrasonic welding of cover 151 to connector module 112 may eliminate the need to use medical grade adhesive to secure radio-opaque marker 60, MBCs 191, 193, 195 and 197 and separate feedthrough wires (not shown) to connector module 112, as well as providing other advantages described hereinabove. FIG. 6 shows a side view of medical device 100 of FIG. 5.

Figure 7:
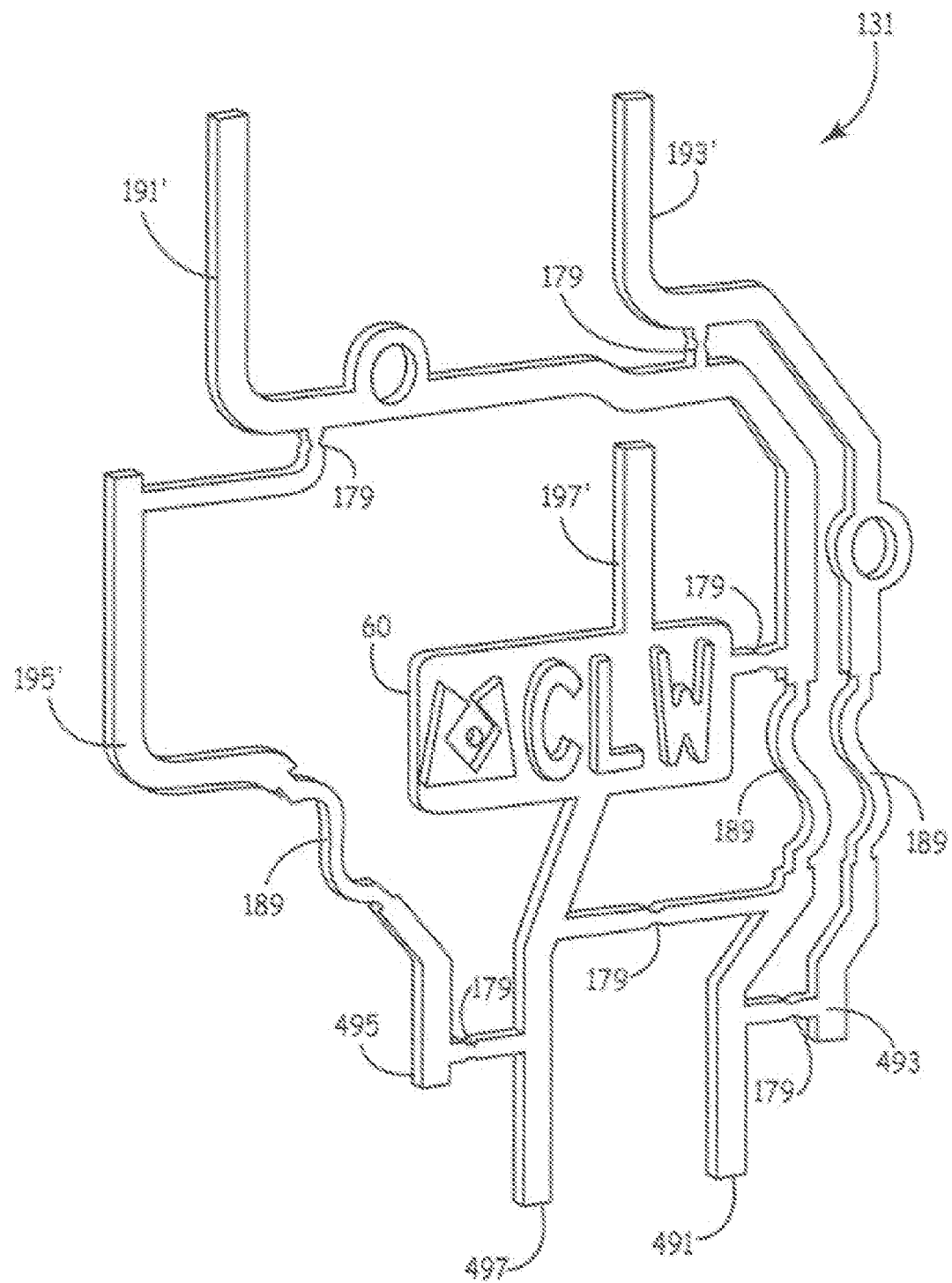
FIG. 7 is a perspective view of the connector ribbon of the present invention.

FIG. 7 shows a perspective view of another embodiment of ribbon connector 131 of the present invention, where strain relief members 189 are shown in greater detail than in FIGS. 5 or 6. Ribbon connector 131 is an interconnect ribbon for connecting feedthrough pins 291, 293, 295 and 297 to MBCs 191, 193, 195 and 197, and owing to its construction provides radio-opaque marker 60 and strain relief members 189 at substantially no additional cost.

Ribbon connector 131 is most preferably formed of 316 L stainless steel, but may also be formed of other corrosion resistant biocompatible metals such as other types of stainless steel, titanium, niobium, tantalum, tungsten, gold, platinum, palladium, alloys or combinations of the foregoing metals, or other suitable metals. It is preferred to form ribbon connector 131 by photo-lithographic means where a resist is placed on a metal sheet having an appropriate structural configuration or shape, the sheet is exposed to light, portions of the sheet masked by the resist are hardened, and portions of the sheet not covered by resist are etched away using an appropriate acid. TECH ETCH, INC. of Plymouth, Mass. provides photolithographic etching services suitable for forming ribbon connector 131 of the present invention.

The thickness of the sheet from which ribbon connector 131 is formed most preferably ranges between about 0.004 and about 0.006 inches, although other thickness obviously fall within the scope of the present invention. In contrast, most prior art feedthrough wires have thicknesses of at least about 0.014 inches. Once the photolithographic and etching process has been completed, it is preferred that ribbon connector 131 be bent into its desired final configuration while being emplaced in recess 147, and also while MBCs 191, 193, 195 and 197 and feedthrough pins 291, 293, 295 and 297 are laser or resistance welded to corresponding ribbon connector contacts 191', 193', 195', 197' and 491, 493, 495 and 497. Emplacement, bending and welding of connector ribbon 131 occur before cover 151 is emplaced in recess 147 and ultrasonically welded to connector module 112. Additionally, bridges 179 disposed between adjoining contacts and ribbons of ribbon connector 131 are severed prior to attachment of cover 151 to connector module 112 and after connector ribbon 131 has been welded to corresponding MBCs and feedthrough pins.

Ribbon connector 131 of the present invention provides the advantages of: (a) eliminating the step of hand forming feedthrough wires; (b) permitting or facilitates automation of final assembly of IMDs; (c) providing strain relief for feedthrough connections at substantially no extra cost; (d) providing radio-opaque markers at substantially no extra cost; (d) permitting the design and manufacture of reduced thickness or profile IMDs.

The above described methods and apparatus for attaching covers or lids to a connector or header module for an IMD may be applied to a wide variety of IMDs having a variety of header or connector module or hermetically sealed enclosure configurations. The principle of the present invention may be extended to various permutations and combinations of such components in many different types of IMDs.

A preferred embodiment modular assembly of the present invention will now be described with reference to FIGS. 8, 9 and 10.

Figure 8:
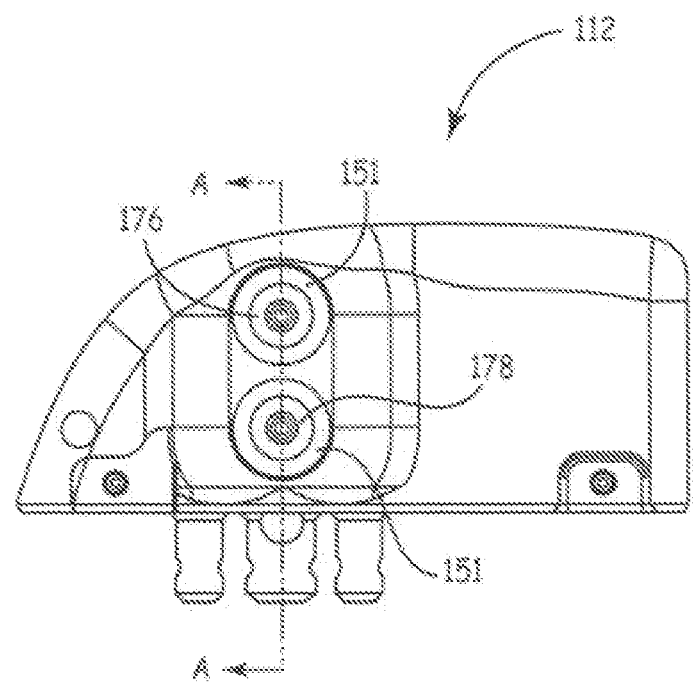
FIG. 8 is an elevational side view of a connector module having a pair of modular access ports according to a preferred embodiment of the present invention.

Referring now to FIG. 8 a connector module 112 having a pair of substantially round modular access ports (see FIG. 10—reference numerals 143, 145) are depicted. A pair of washer-type lids 151 adapted to be ultrasonically welded around the periphery portions thereof surround a portion of a central grommet unit 176, 178 disposed in the access ports 143, 145. The materials used to fabricate the lids 151 should be susceptible of ultrasonic welding to the periphery of the access ports 143, 145 in accordance with the description of the other embodiments of the present invention. As described and depicted with respect to other embodiments of the present invention, a single major lid 151 may have two round washer-type lids coupled thereto; however, in this preferred embodiment, the lids 151 are modular. The two or more lids 151 depicted in FIG. 8 may be simultaneously ultrasonically welded to the connector 112.

Figure 9:
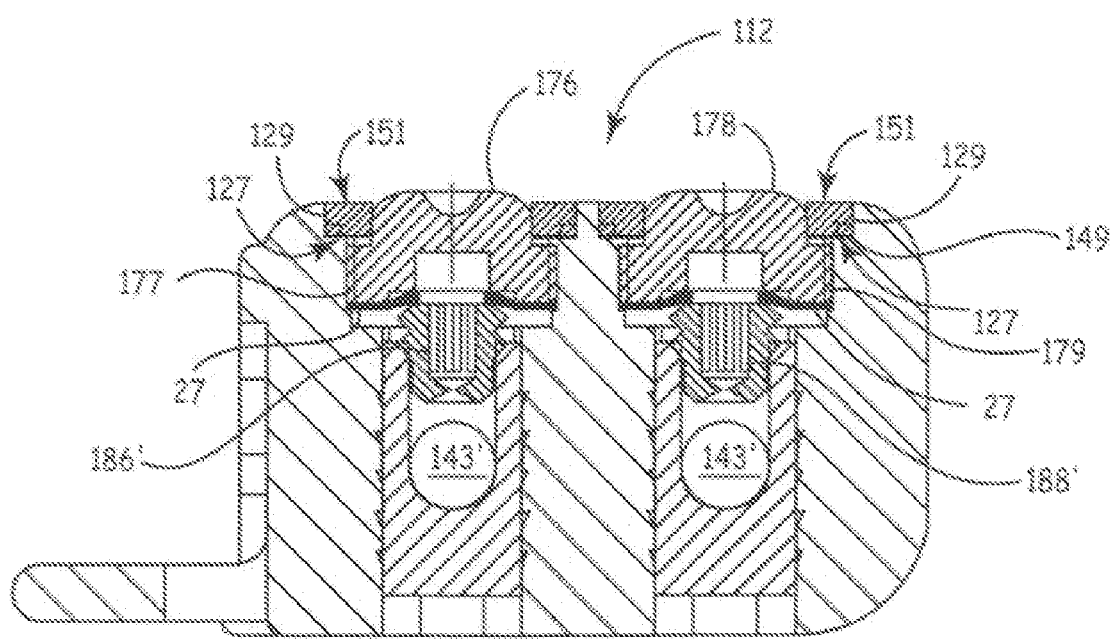
FIG. 9 is a cross-sectional view taken along the line A—A of FIG. 8 and depicting the pair of modular access port assemblies and the cavity adjacent each access port, wherein each access port has a resilient grommet member disposed between a washer-type lid and an adjustable setscrew; in addition, an optional halt ring is depicted retaining the setscrew and abutting a shoulder member of the cavity.

FIG. 9 is a cross-sectional view taken along the line A—A of FIG. 8 and depicting the pair of modular access port assemblies and the medical lead receiving ports 182, 184 adjacent each access port 143, 145 (see FIG. 10), wherein each access port has a resilient grommet member 176, 178 each compressibly coupled by a single washer-type lid 151 an annular shoulder or step 27 and an adjustable setscrew 186', 188'; in addition, an optional halt ring 177, 179 is depicted retaining a setscrew 186', 188' and abutting the shoulder member 27 of the cavity 143, 145.

Figure 10:
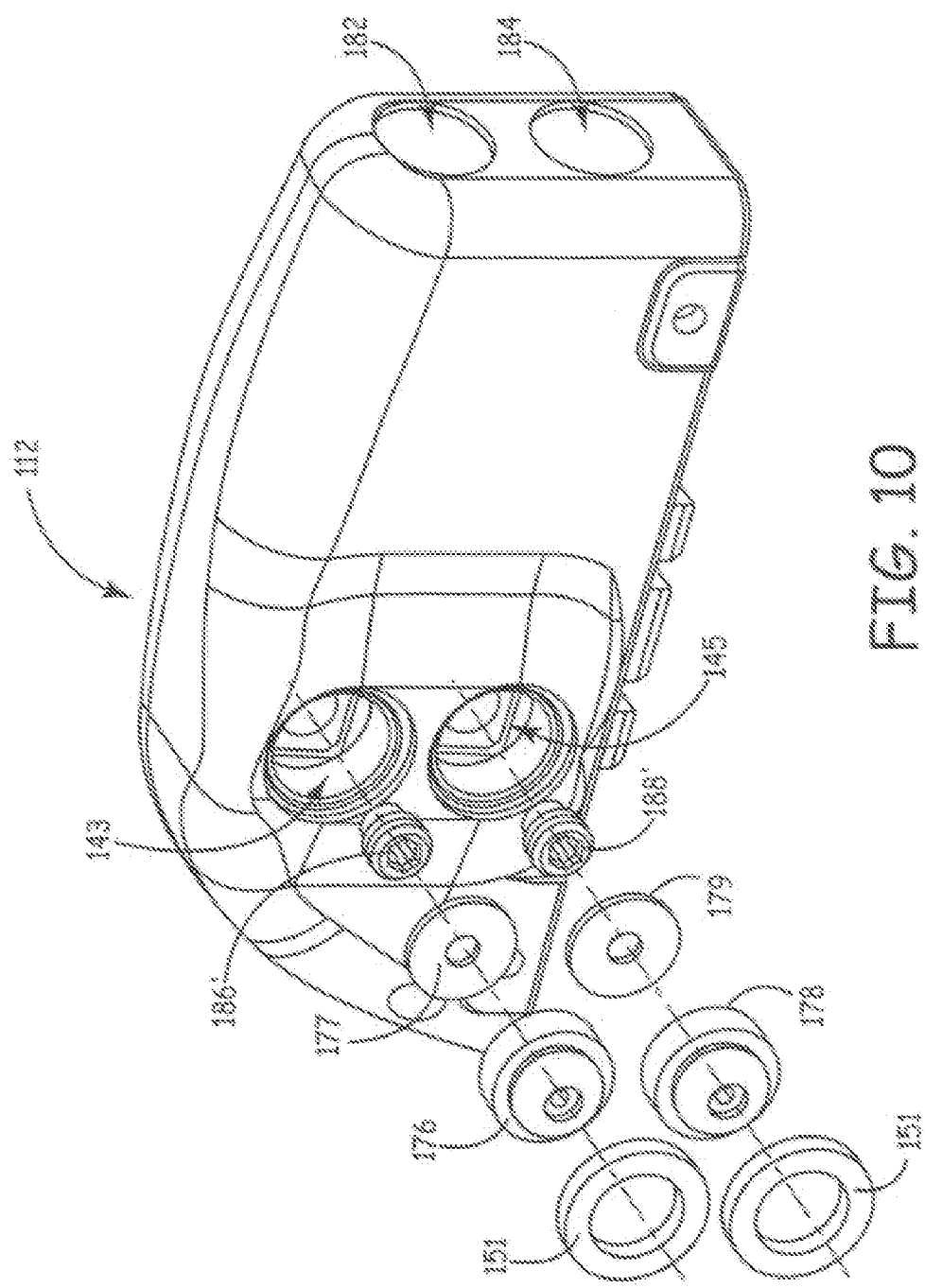
FIG. 10 is a combination perspective and exploded view of the connector module depicted in FIGS. 8 and 9 which illustrates a preferred order for each of the modular access port assemblies.

FIG. 10 is a combination perspective and exploded view of the connector module 112 depicted in FIGS. 8 and 9 which illustrates a preferred order for each of the modular access port assemblies. That is, setscrews 186', 188', optional halt rings 177, 179, resilient grommets 176, 178 and washer-type lids 151 aligned with the ports 143, 145. While not illustrated in FIG. 10 the medical lead receiving ports 182, 184 couple to the ports 143, 145 so that the setscrews 186', 188' firmly contact a portion of a proximal end portion of a medical lead (not shown) when adjusted with a manual wrench or the like (not shown).

Figure 11:
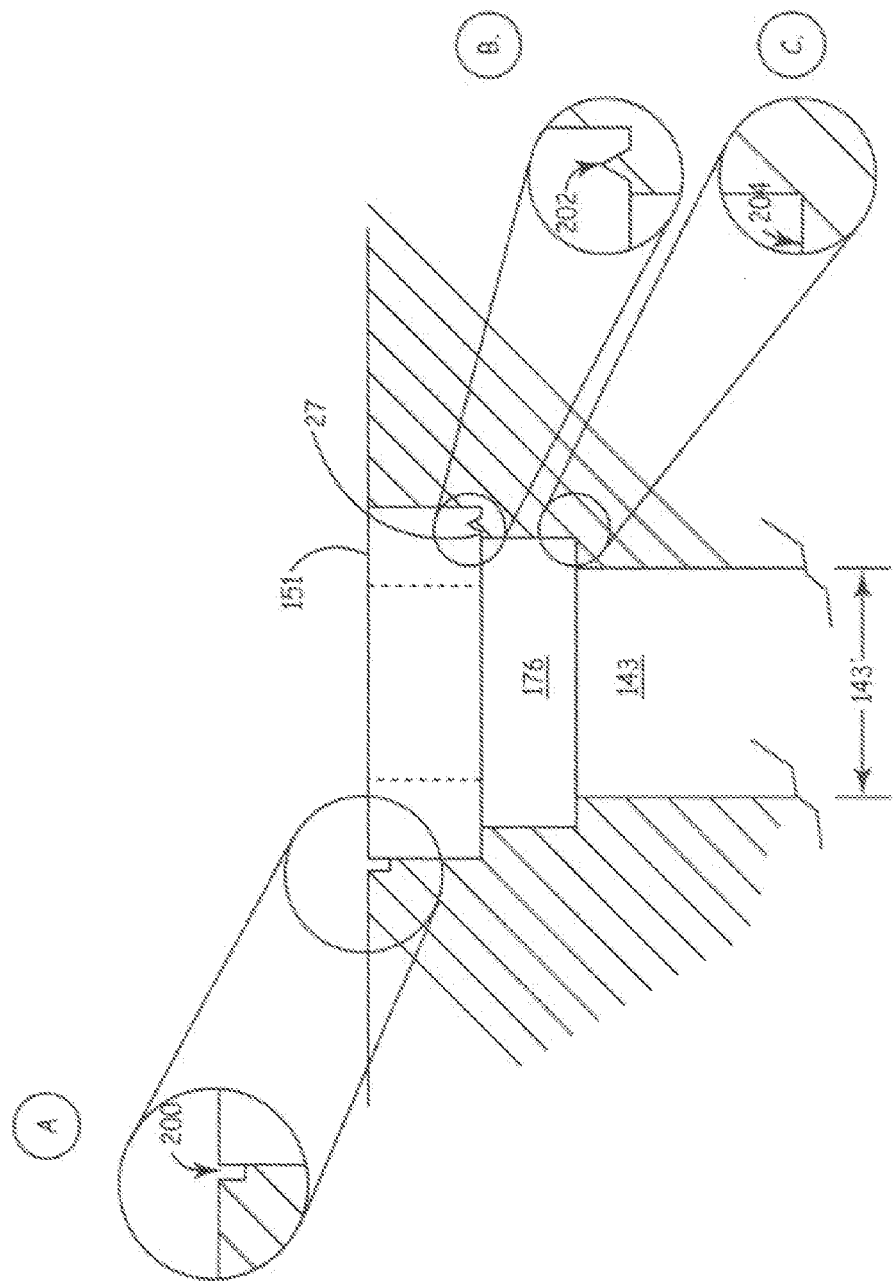
FIG. 11 is an elevational view in cross section with three portions exploded (denoted as views "A" "B" and "C") illustrating a lid member disposed in a first portion of a port in an IMD, a compressible member disposed in a second portion of the port and wherein view "A" depicts a flash-reducing annular slot formed in the exterior surface of the IMD for absorbing thermoplastic material formed during near-field ultrasonic welding, view "B" depicts an energy director member disposed on an annular shelf member for enhancing a far-field ultrasonic weld, and view "C" depicts an annular mechanical stop structure against which the resilient member is compressed by the lid during ultrasonic welding.

FIG. 11 is an elevational view in cross section with three portions exploded (denoted as views "A" "B" and "C") illustrating a lid member 151 disposed in a first portion of a port 143 in an IMD, a compressible member 176 disposed in a second portion of the port 143 which is narrower than the first portion. View "A" depicts a flash-reducing annular slot 200 formed in the exterior surface of the IMD for absorbing thermoplastic material formed during near-field ultrasonic welding. View "B" depicts an energy director member 202 disposed on an annular shelf member 27 for enhancing a so-called far-field ultrasonic weld. View "C" depicts an annular mechanical stop structure 204 against which the resilient member 176 is compressed by the lid 151 during ultrasonic welding. As noted elsewhere in this disclosure, and as known in the art, the energy director member 202 may have a wide variety of shapes and sizes designed to facilitate the ultrasonic weld. The embodiment of the present invention depicted in FIG. 11 is adapted for use as a refill port of an implantable drug delivery pump wherein the port 143 couples to fluid reservoir 143'.

Figure 12:
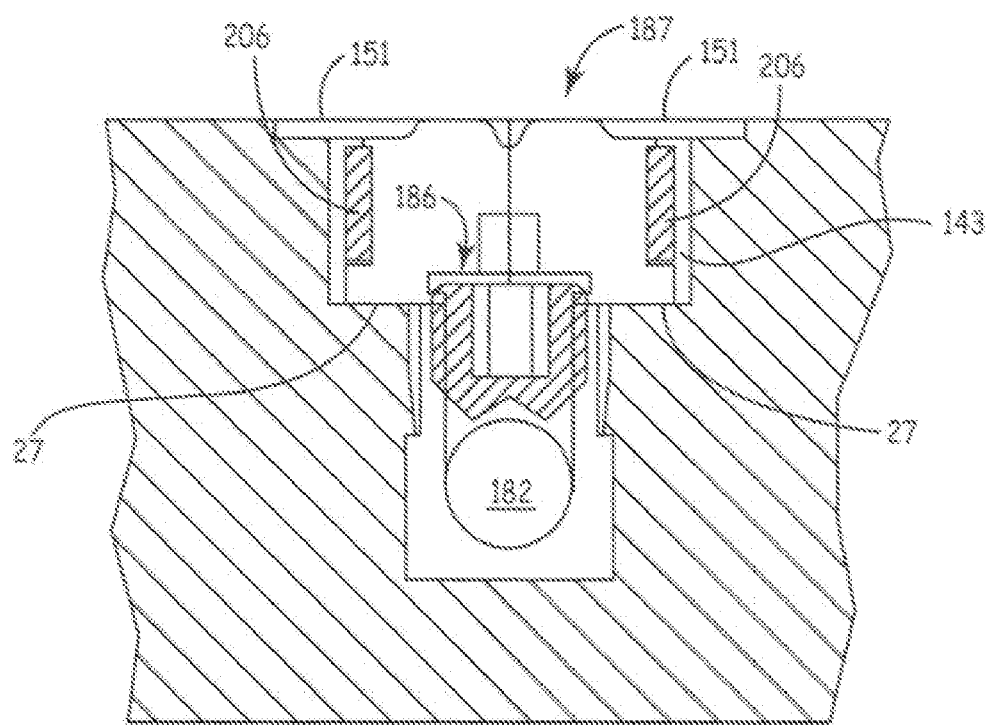
FIG. 12 is an elevational view in of another embodiment of the present invention wherein a two-piece grommet assembly with a band member wrapped around the circumference of the grommet assembly is disposed in a port and compressibly retained by a lid member configured to topography of the grommet assembly.

FIG. 12 is an elevational view in of another embodiment of the present invention wherein a two-piece grommet assembly 187 with a band member 206 wrapped around the circumference of the grommet assembly 187 is disposed in a port 143 and compressibly retained by the lid member 151 configured around the central opening of the lid 151 to follow the topographical contours of the grommet assembly 187.

Figure 13A:
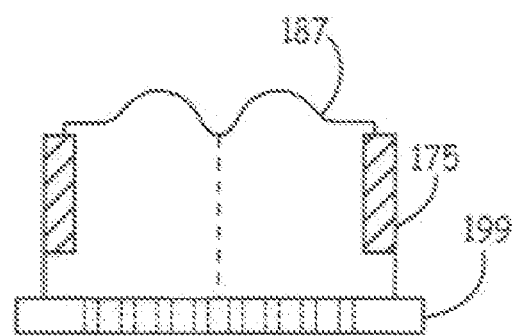
FIG. 13 comprises three views of an embodiment of the present invention adapted for use as a septum of an implantable drug pump; namely, view "A" which is an elevational view in cross section taken along the line 13—13 (of view "B") and depicting the two-piece grommet assembly of FIG. 12 abutting a perforated disk-shaped member, view "B" is a plan view of the assembly depicted in view "A" and view "C" is a plan view of the perforated disk-shaped member.
Figure 13B:
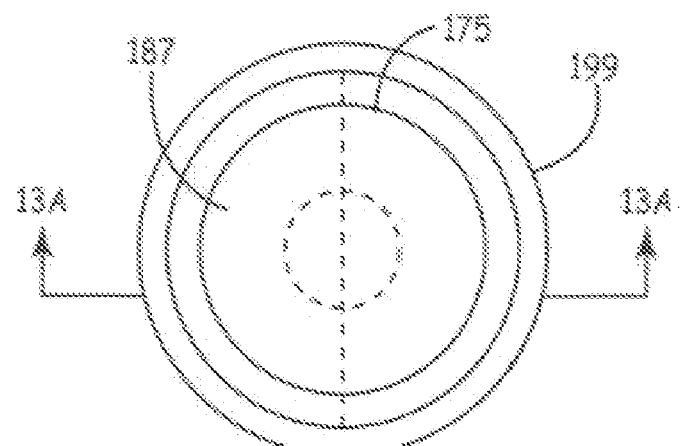
Figure 13C:
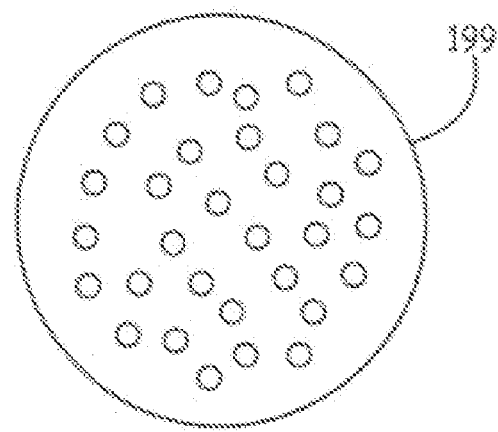

FIG. 13 comprises three views of an embodiment of the present invention adapted for use as a septum of an implantable drug pump; namely, view "A" which is an elevational view in cross section taken along the line 13—13 (of view "B") and depicting the two-piece grommet assembly 187 of FIG. 12 abutting a perforated disk-shaped perforated member 199. View "B" is a plan view of the assembly depicted in view "A" and showing the perforated member 199, the grommet assembly 187 and the lid 151. View "C" is a plan view of the perforated disk-shaped member 199 illustrating the plurality of syringe-admitting apertures formed therein.

Figure 14:
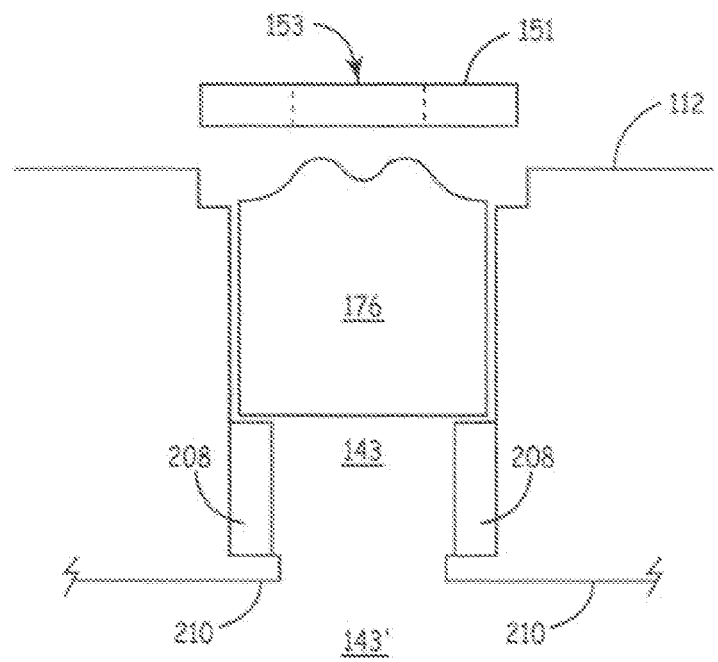
FIG. 14 is an elevational view in cross section with one part exploded and depicting a lid member having a central opening, a resilient grommet (or septum) member abutting the lid and an annular sleeve supporting the grommet (or septum) member.

FIG. 14 is an elevational view in cross section with one part exploded (151) and depicting a lid member 151 having a central opening 153, a resilient grommet (or septum) member 176 abutting the lid 151 and an annular sleeve 208 supporting the grommet (or septum) member 176 at a first end and abutting an annular step (or mechanical stop) member 210. In this embodiment, the port 143 fluidly couples to the fluid reservoir 143'.

Figure 15A:
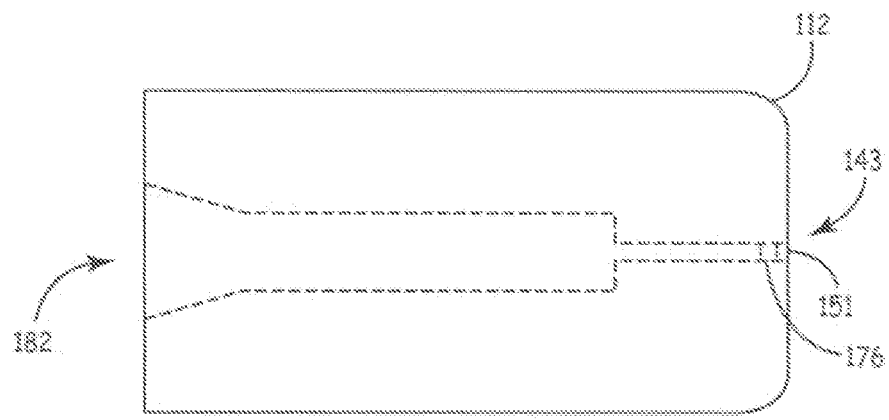
FIG. 15 is a diagram comprising two views, view "A" which is a cross sectional view of a connector module of an IMD having a major connector port coupled to a minor "pull tool" port and wherein a lid member compressibly retains a resilient grommet (or septum) member in the minor port (a mechanical stop member is not depicted) and view "B" which depicts a heuristic representation of a proximal end of a medical electrical lead adjacent an thin, elongated pull tool adapted to be inserted through the minor port to engage the medical lead and then is reversed to advance the medical lead into the major port.
Figure 15B:
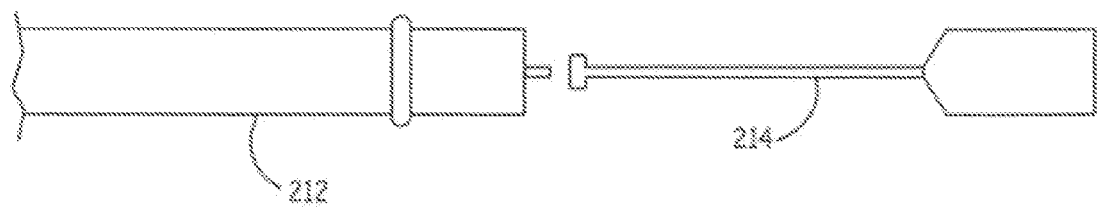

FIG. 15 is a diagram comprising two views, view "A" which is a cross sectional view of a connector module 112 of an IMD having a major connector port 182 coupled to a minor "pull tool" port 143 and wherein a lid member 151 compressibly retains a resilient grommet (or septum) member 176 in the minor port 143 (a mechanical stop member is not depicted) and view "B" which depicts a heuristic representation of a proximal end of a medical electrical lead 212 adjacent an thin, elongated pull tool 214 adapted to be inserted through the minor port 143 to engage the medical lead 212 and then is reversed to advance the medical lead 212 fully into the major port 143.

The preceding specific embodiments are illustrative of the practice of the invention. It is understood therefore that other expedients and equivalents of disclosed components or functions known to those of skill in the art or otherwise disclosed herein may be employed in practicing the invention without departing from the invention or the scope of the following claims.

In the following claims, means-plus-function clauses are intended to cover the structures described herein as performing the recited function and not only structural equivalents but also equivalent structures. For example, although a nail and a screw may not be structural equivalents in that a nail employs a cylindrical surface to secure wooden parts together, whereas a screw employs a helical surface, in the environment of fastening wooden parts, a nail and a screw are equivalent structures.

We claim:

1. A device, comprising:
   a thermoplastic connector module configured to couple to an implantable medical device;
   a first cavity formed in the thermoplastic connector module of an implantable medical device, said first cavity defining a surface opening in the thermoplastic connector module and said surface opening having a geometric periphery;
   a pierceable resilient member disposed in the first cavity; and
   a perforated thermoplastic lid ultrasonically welded to the geometric periphery of the surface opening and abutting the pierceable resilient member so that said pierceable resilient member is compressed; and one of a flash-reducing feature and an energy director structure located intermediate a portion of the lid and an opposing portion of the surface opening and further comprising a header module having a major connector port formed therein;

wherein the first cavity comprises a minor port formed in the header module and said first cavity is aligned with a longitudinal axis of the major connector port and wherein the major connector port is configured to receive a proximal end of a medical electrical lead.

2. A device according to claim 1, wherein the perforated lid has a substantially continuous ultrasonic weld formed between the surface opening and the lid.

3. A device according to claim 1, wherein the perforated lid is a washer member.

4. A device according to claim 1, further comprising: a connector fastening member disposed within the first cavity.

5. A device according to claim 1, further comprising:
an interior annular shoulder member disposed within the first cavity and wherein a portion of the resilient member abuts the interior annular shoulder member of the first cavity so that said resilient member is retained at a predetermined elevation relative to the surface opening.

6. A device according to claim 1, wherein an energy director member is disposed between the periphery of the perforated lid and the periphery of the opening.

7. A device according to claim 1, wherein the connector module comprises a header unit for an implantable medical device and the implantable medical device consists of one of the group:
an implantable cardioverter-defibrillator (ICD), a pacemaker, a defibrillator, an implantable nerve stimulator, an implantable muscle stimulator, a data logger.

8. A device according to claim 1, wherein the geometric shape of the perforated lid is: a round shape, a square shape; an oval shape; a polygon shape or a rhomboid shape.

9. A device according to claim 1, wherein the resilient member is adapted to temporarily receive a thin elongated pull tool adapted to engage the proximal end of the medical electrical lead.

10. A device according to claim 1, wherein the resilient member is a substantially disk-shaped member and wherein the resilient member further comprises:
a pair of abutting parts having a part interface therebetween; and
a band surrounding the pair of abutting parts to retain the pair of abutting parts in mutual sealing contact so that an adjustment instrument temporarily inserted into the part interface does not permanently disrupt the mutual sealing contact between the pair of abutting parts.

11. A device according to claim 10, wherein the pair of abutting parts has a central portion of reduced thickness relative to a non-central portion of the pair of abutting parts.

* * * * *